June 23, 1953 M. L. WHISLER Plant Pat. 1,199
ROSE PLANT
Filed Sept. 26, 1951
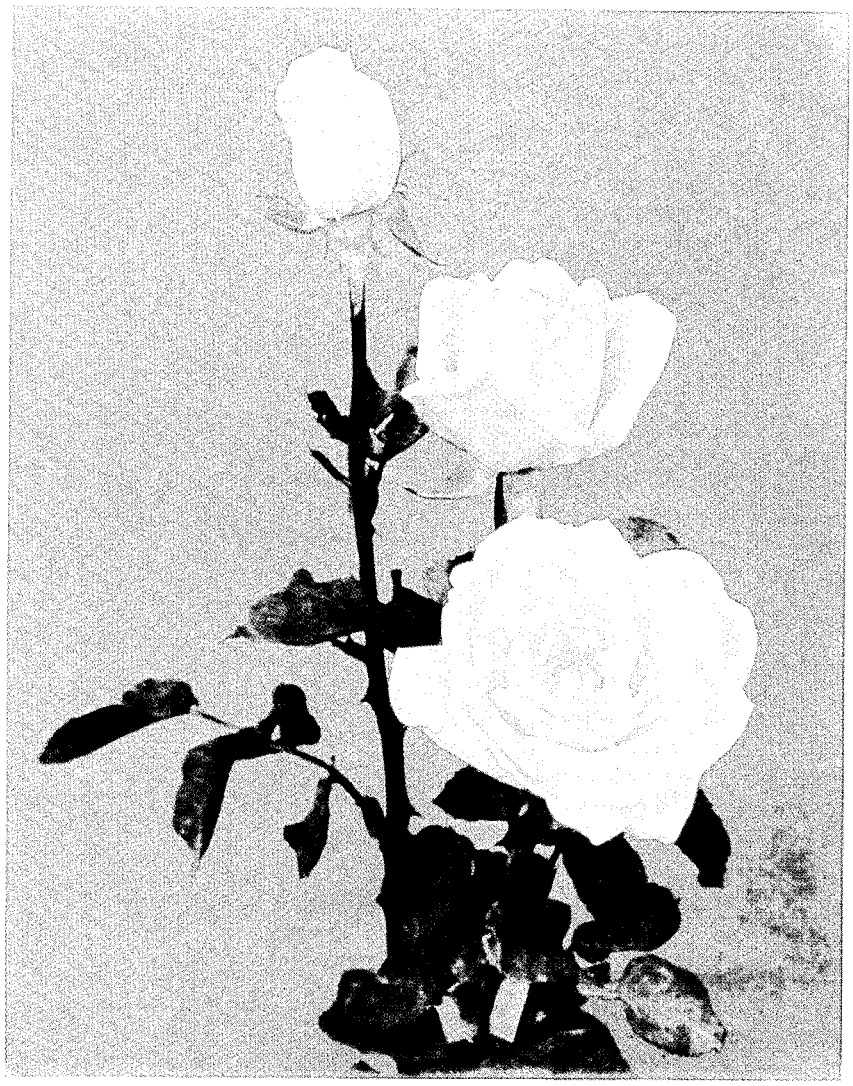
Inventor.
M. L. Whisler
By: Robb & Robb
Attorneys.

Patented June 23, 1953

Plant Pat. 1,199

UNITED STATES PATENT OFFICE 1,199

ROSE PLANT

Milton L. Whisler, Van Nuys, Calif., assignor to Germain's, Inc., Van Nuys, Calif., a corporation of California Application September 26, 1951, Serial No. 248,295

1 Claim. (Cl. 47—61)

The present invention relates to a new and distinct variety of rose plant of the hybrid tea class, originated by me by crossing the variety "Golden Rapture" (unpatented) × [a cross of an unnamed and unpatented seedling × the variety "Joanna Hill" (unpatented)].

As the result of this breeding, I have produced a new variety which is substantially different from its parents as well as from other varieties of this class, but which resembles the variety "Diamond Jubilee" (Plant Patent No. 824) more than any other, yet is distinctly different therefrom.

The primary features of novelty and distinctiveness of the new variety are evidenced by its vigorous growth, heavy canes, long and strong stems, long pointed buds, and the profuse blooming habit of its basically yellow flowers which vary in general color tonality from Mimosa Yellow in the newly open flower, to Empire Yellow in the 3-days open flower, with the outer areas of the petals modified by fading to a creamy white, and at times tinted Shrimp Pink on both the inside and outside surfaces of the petals.

Asexual reproduction of this new variety by cuttings, grafting and budding at Van Nuys, California, shows that the foregoing characteristics come true and are established and transmitted through succeeding propagations.

The accompanying drawing shows specimens of the flowers and foliage of the new variety in different stages of development.

The following is a detailed description of the new variety, with color terminology in accordance with the Horticultural Color Chart of the British Color Council, except where general color terms of ordinary dictionary significance are obvious:

Type: Half hardy; bush; outdoor; seedling; for cut flowers and for garden decoration.
Class: Hybrid tea.
Breeding: Seedling.
*Seed parent.*—"Golden Rapture."
*Pollen parent.*—A cross of an unnamed seedling × "Joanna Hill."
Propagation: Holds its distinguishing characteristics through succeeding propagations by cuttings, grafting and budding.

*Flower*

Locality where grown and observed: Van Nuys, California.
Flowers borne: Singly to stem; on strong, long stems.
Quantity of bloom: Free; outdoors.

Continuity: Continuous.
Fragrance: Slight; nutty.
Bud:
*Peduncle.*—Medium length; heavy; stiff; reddish green; few red hairs.
*Before calyx breaks.*—Size—medium. Form long; pointed; with foliaceous appendages on the surface of the bud; with slender, much cut foliaceous parts extending beyond the tip of the bud equal to ½ of its length. Color—light green.
*As calyx breaks.*—Color—Canary Yellow, Plate 2/3, to a creamy white; petal edges at times tinted Shrimp Pink, Plate 616/3.
*As first petal opens.*—Size—large. Form—long; pointed. Color: outside—Canary Yellow, Plate 2/3, shaded to creamy white at petal edges; inside—Mimosa Yellow, Plate 602/3; at times petal edges tinted Shrimp Pink, Plate 616/3.
*Opening.*—Opens up well, but is somewhat retarded from opening by cold weather.
Bloom:
*Size, when fully open.*—Large; 4 inches to 5 inches.
*Petalage.*—Double, from 35 to 40 petals; arranged regularly.
*Form.*—Cupped at first; becoming open-cupped; petals being at first cupped; becoming later, at maturity, flat-cupped.
Petals: Thick; soft; with inside and outside satiny.
*Shape.*—Outside—round; intermediate—obovate.

This description of a newly opened flower was made from a rose grown outdoors in the month of August, at Van Nuys, California:

*Color.*—Outside petal: outside surface—Canary Yellow, Plate 2/3; inside surface—Mimosa Yellow, Plate 602/3. Intermediate petal: outside surface—Straw Yellow, Plate 604/3; inside surface—Mimosa Yellow, Plate 602/2. Inner petal: outside surface—Straw Yellow, Plate 604/2; inside surface—Mimosa Yellow, Plate 602/2.

This description was made from a rose that was open for three days outdoors in the month of August, at Van Nuys, California:

*Color.*—Outside petal: outside surface—Empire Yellow, Plate 603/3; inside surface—Empire Yellow, Plate 603/3. Inside petal: outside surface—Empire Yellow, Plate 603/3, washed with Shrimp Pink, Plate 616/3; inside surface—Empire Yellow, Plate 603/3, washed with Shrimp Pink, Plate 616/3.

The colors referred to in the foregoing are more particularly applicable to the areas near the bases of the flower petals. Toward the outer area of the petals, these colors may be modified by fading to a creamy white or light creamy white color, and sometimes both the inside and outside surfaces of the petals may be washed or tinted Shrimp Pink, Plate 616/3. The wash or tinting is most prominent near the petal edges. However, the tinting and fading reactions are usually dependent upon weather conditions. Warm days and cool nights in the fall season tend to intensify these characteristics.

*General color effect.*—Newly opened flower—Mimosa Yellow, Plate 602/3. Three days open—Empire Yellow, Plate 603/3, washed with Shrimp Pink, Plate 616/3.

*Behavior.*—Drop off cleanly.

*Flower longevity.*—On bush in garden—4 days in August. Cut roses, grown outdoors, kept at living room temperature—3 days in August.

*Reproductive organs*

Stamens: Many; arranged regularly about pistils.

Filaments: Medium length; most with anthers. Color—Empire Yellow, Plate 603/2.

Anthers: Medium size; all open at once. Color—white.

Pollen: Moderate; yellow.

Pistils: Medium number.

Styles: Uneven; long; medium heavy; loosely bunched.

Stigma: White.

Ovaries: Some protruding from calyx.

Hips: Short; flat; greenish yellow; smooth; walls thick, dry.

Sepals: Falling soon. Color—light grey-green.

*Plant*

Foliage:

*Leaves.*—Compound of five leaflets; normal abundance; medium to large; moderately heavy; glossy.

*Leaflet.*—Shape—Oval, with apex acute. Base—round. Margin—doubly serrate.

*Color.*—Mature: upper surface—dark green; under surface—light green. Young: upper surface—light green; under surface—green-bronze.

*Rachis.*—Medium weight. Upper side—grooved; hairy. Under side—smooth.

*Stipules.*—Medium length; wide; with short points turning out at an angle of more than 45°.

*Disease.*—Resistant to mildew, as determined by comparison with other varieties grown under comparable cultural conditions at Van Nuys, California.

Growth:

*Habit.*—Upright; much branched.

*Growth.*—Vigorous.

*Canes.*—Heavy.

*Main stems.*—Color—dull green. Thorns—several; medium length; straight; with long, broad base. Prickles—none. Hairs—none.

*Branches.*—Color—dull green. Thorns—several; medium length; straight; with broad base. Prickles—none. Hairs—none.

*New Shoots.*—Color—dull greenish bronze. Thorns—several; medium length; hooked downward; with long, narrow base. Prickles—none. Hairs—none.

I claim:

A new and distinct variety of rose plant of the hybrid tea class, substantially as herein shown and described, characterized as to novelty by its vigorous growth, heavy canes, long and strong stems, by its long pointed buds, and by the profuse blooming habit of its flowers of yellow color near the bases of the petals, shading to creamy white near the outer edges of the petals, and sometimes washed or tinted Shrimp Pink on both the inside and outside surfaces of the pedals.

MILTON L. WHISLER.

No references cited.